(19) United States Patent [19]
Cantrell

[11] Patent Number: 4,886,920
[45] Date of Patent: Dec. 12, 1989

[54] PROCESS FOR PREPARING AROMATIC FLUORIDES

[75] Inventor: Gary L. Cantrell, Belleville, Ill.

[73] Assignee: Mallinckrodt, Inc., St. Louis, Mo.

[21] Appl. No.: 177,986

[22] Filed: Apr. 5, 1988

Related U.S. Application Data

[63] Continuation-in-part of Ser. No. 34,351, Apr. 6, 1987, abandoned.

[51] Int. Cl.$^4$ .................. C07C 17/22; C07C 25/13; C07C 25/18; C07D 213/02
[52] U.S. Cl. .................................. 570/141; 534/558; 534/565; 534/559; 534/581; 570/123; 570/127
[58] Field of Search .................. 534/565, 559, 681; 570/141

[56] References Cited

U.S. PATENT DOCUMENTS

| | | | |
|---|---|---|---|
| 2,606,183 | 4/1952 | Head et al. | 534/565 |
| 2,861,984 | 11/1958 | Gordon et al. | 534/565 |
| 3,160,623 | 12/1964 | Anello et al. | 534/565 |
| 3,405,116 | 10/1968 | Ischer | 534/581 |
| 3,406,161 | 10/1968 | Dore et al. | 534/581 |
| 3,471,511 | 10/1969 | Kollonitsch | 534/565 X |
| 3,915,953 | 10/1975 | Mori et al. | 534/559 X |
| 4,096,196 | 6/1978 | Boudakian | 534/565 |

FOREIGN PATENT DOCUMENTS

| | | | |
|---|---|---|---|
| 214068 | 3/1987 | European Pat. Off. | 534/565 |
| 109688 | 1/1961 | Fed. Rep. of Germany | 534/565 |
| 59-6723 | 4/1984 | Japan | 534/565 |
| 61-1789 | 8/1986 | Japan | 534/565 |
| 215920 | 7/1968 | U.S.S.R. | 534/565 |

OTHER PUBLICATIONS

Kirk–Othmer, "Encyclopedia of Chemical Technology", 2nd Ed., vol. 11, pp. 174 and 175; vol. 19, pp. 242 and 247 (1966).
Fisher, E., Ber. 10, 1334 (1877).
Curtius, T., Ber. 26, 1263 (1893).
Wohl, A., and Schiff, H., Ber. 33, 2741 (1900).
Griess, P., Ber. 9, 1659 (1876).
Grandmougin, E., Ber. 40, 422 (1907).
Forster, M. O. and Withers, J. C., *J. Chem. Soc.,* 103 266 (1913).
Clusius, K., and Weisser, H. R., *Helv. Chim. Acta,* 35, 1548 (1952).
Tilden, W. A. and Miller, J. H., *J. Chem. Soc.* 63 256 (1893).
Griess, P., Ber. 19, 313 (1886).
Fischer, E. Ber. 9, 880 (1876); *ibid,* 1840.
Wallach, O., and Tewes, A. *Chem. Zentr.,* 1899, II, 1050.
Smith, P. A. S., and Brown B. B., *J. Am. Chem.,* Soc., 73, 2438 (1951).
L'Abbe, G., *Chem. Rev.,* 69, 345 (1969).
Ng, J. S., Katzenellenbogan, J. A. and Kilbourn, M. R., *J. Org. Chem.,* 46, 2520 (1981).
Mulvey, D. M., DeMarco, A. M. and Weinstock, L. M., *Tet. Lett.,* No. 16, 1419 (1978).
Strecker, A. and Romer, A. Ber. 4, 784 (1871).
Fischer, E. Ber. 8, 589 (1875); ibid, 1005; ibid, 1691.
Saunders et al., Aromatic Diazo Compounds, 3rd Ed., pp. 725–730.
Wannagat et al., Jagrg. 88, Nr. 12 (1955), pp. 1839–1846.
Fitzpatrick et al., *J. Chem. Soc. Perkin Trans. II,* pp. 927–932 (1984).

*Primary Examiner*—Floyd D. Higel
*Attorney, Agent, or Firm*—Bernard, Rothwell & Brown

[57] ABSTRACT

An improved process is disclosed for preparing aromatic fluorides by diazotization-fluorination in hydrogen fluoride wherein the diazotized reaction mixture includes an oxidizing agent such as nitrosonium ion from excess diazotization agent. The improvement includes, prior to decomposing the diazonium fluoride, adding to the diazotized reaction mixture a member selected from hydrazine, aromatic hydrazine, semi-carbazide, thio-semicarbazide, acid salts thereof, sulfur dioxide, sodium sulfate, and sodium bisulfite to remove at least a portion of the oxidizing agent. Urea was found to be ineffective.

15 Claims, No Drawings

PROCESS FOR PREPARING AROMATIC FLUORIDES

CROSS-REFERENCE TO RELATED APPLICATIONS

This is a continuation-in-part of the application Ser. No. 034,351, filed Apr. 6, 1987 abandoned.

BACKGROUND OF THE INVENTION

This invention relates to an improved process for preparing aromatic fluorides by diazotization-fluorination in hydrogen fluoride.

Preparation of aromatic fluorides from corresponding aromatic primary amines by diazotization-fluorination processes is well known. In such processes, (A) an aromatic primary amine is diazotized in a reaction mixture comprising (i) a reaction medium consisting essentially of hydrogen fluoride, (ii) the amine and (iii) a nitrosonium ion-containing or -generating diazotization agent under reaction conditions such that the resulting reaction mixture comprising the resulting aromatic diazonium fluoride typically further comprises one or more oxidizing agents, e.g. nitrous acid or other nitrosonium ion-containing or -generating composition, whereby the reaction mixture has a positive oxidation potential as shown by its production of oxidant-indicating blue color on test paper impregnated with starch and potassium iodide, and (B) the aromatic diazonium fluoride is decomposed at elevated temperature in the resulting reaction mixture to nitrogen and the aromatic fluoride.

The presence of oxidizing agent, such as excess nitrosonium ion, in the reaction mixture wherein the diazonium fluoride is being decomposed results in substantially increased corrosion, low yields of the desired aromatic fluoride, and formation of undesired by-products such as resinous material and tar. The presence of oxidizing agent in the reaction mixture results from, for example, charging a nitrosonium ion-containing or -generating diazotization agent in an amount in excess of the amount stoichiometrically required for diazotization of the entire amount of aromatic primary amine employed. Such an excess is often intentionally employed to maximize the amount of amine converted to diazonium fluoride. In other instances, such excess per se is not intentionally employed; rather, it is desired merely to convert the entire amount of the amine, but due either to loss of some of the diazotization agent (e.g., loss of some nitrous acid as NO or $NO_2$) or one or more other reasons it is necessary to test the reaction mixture as with starch-potassium iodide paper to determine whether a sufficient amount of the diazotization agent has been added. Since such test merely shows the presence or absence of oxidizing agent (e.g. nitrous acid), additional diazotization agent (e.g. sodium nitrite) is added until the starch-potassium iodide test shows the characteristic oxidant-indicating blue color, corresponding to at least a slight excess of diazotization agent.

Preparation of diazonium salts by reaction of primary aromatic amines with nitrous acid is discussed by Morrison and Boyd, *Organic Chemistry*, 1959, pages 570–571. According to Morrison and Boyd, nitrous acid is generated in the presence of the amine by the reaction between sodium nitrite and a mineral acid, "usually" hydrochloric acid or sulfuric acid; diazotization is "generally" carried out in a way wherein the amine is dissolved or suspended in an "aqueous solution" of the mineral acid and excess sodium nitrite is added, thereby generating excess nitrous acid which interferes with subsequent reactions of the diazonium salt; and accordingly the excess nitrous acid is "destroyed" by the addition of urea, which reacts with nitrous acid to form nitrogen, carbon dioxide and water.

Unfortunately, in the course of attempting to solve the problems which are substantially overcome by this invention, addition of urea to a diazotized reaction mixture containing at least one nitrosonium-ion based oxidizing agent in a reaction medium consisting essentially of hydrogen fluoride was found to be ineffective for destroying the oxidizing agent. Other agents which proved to be ineffective for destroying the oxidizing agent are hydroxylamine and its salts, metabisulfides and iron compounds. Sulfamic acid, an agent which has largely supplanted the use of urea as a $NO^+$ quencher in aqueous systems, was found to be ineffective in HF due to its poor solubility and resulting slow reaction rate. Phosphorous chloride was found to be an effective agent, but results in unwanted chloride-containing by-products such as HCl. The present invention effectively solves the problems associated with destroying the oxidizing agent in diazotized reaction mixtures without resulting in unwanted by-products.

Various compounds which were thought to be nitrous acid scavengers were compared in Fitzpatrick et al., *J. Chem. Soc. Perkin Trans. II* p. 927–932 (1984), including urea, hydroxylamine, hydrazoic acid, hydrazine, sulphamic acid, and 4-nitroaniline. The tests were conducted over a range of acidity of 0–1.5M $HClO_4$ to determine which compounds were the best nitrous acid scavengers. The acidity levels tested in the Fitzpatrick article are about a magnitude of about $10^8$–$10^9$ weaker in acidity than the HF solution of a diazotization reaction. It has been found, therefore, that the results of these tests do not help in determining effective nitrous acid scavengers for these reactions. For example, as noted above, urea and hydroxylamine hydrochloride were found to be ineffective and did not react with dilute $NO^+$ in HF. Sulfamic acid powder reacted slowly because of its lack of solubility in HF. Hydrazoic acid, which was listed in the Fitzpatrick article as one of the best nitrous acid scavengers at the acidity levels tested, is very toxic and decomposes at the high acidities found in HF solutions used in diazotization-fluorination reactions. Hydrazinium ion, while listed as a nitrous acid scavenger, is only sparingly soluble in HF. Using nitroanilines, as suggested by the article, complicates the diazotization-fluorination process since the resulting diazonium salts decompose at much higher temperatures, resulting in a toxic, potentially explosive waste. Also, excess nitroaniline that is undiazotized must be eliminated from the HF residue because of its toxicity and established Environmental Protection Agency limits.

Therefore, the problem of destroying excess nitrous acid in HF solution could not be solved by the use of traditional nitrous acid scavengers, since the reaction of these scavengers is unpredictable in the high acidity levels present.

SUMMARY OF THE INVENTION

It has now unexpectedly been found that $SO_2$, hydrazine and other particularly defined compounds are effective for decomposing nitrosonium ion-containing oxidizing agents in diazotized reaction mixtures comprising aromatic diazonium fluoride and a reaction medium consisting essentially of hydrogen fluoride, thereby reducing the oxidation potential of such mixtures.

Surprisingly and unexpectedly, it has been further found that excess amounts of the compounds of this invention can be employed without causing a decrease in the yield of aromatic fluoride obtainable upon decomposition of the diazonium fluoride at elevated temperatures in such reaction mixture.

Generally stated, therefore, the present invention provides an improvement in the above-described, heretofore known diazotization-fluorination process wherein a diazotized reaction mixture comprising an aromatic diazonium fluoride in hydrogen fluoride further comprises at least one nitrosonium ion-containing oxidizing agent. The improvement comprises, prior to decomposing the diazonium fluoride, adding to the diazotized reaction mixture a member selected from the group consisting of hydrazine, aromatic hydrazine, semicarbazide, thiosemicarbazide and acid salts thereof, sulfur dioxide, sodium sulfite and sodium bisulfite. The acid salts of hydrazine, aromatic hydrazine, semicarbazide, and thiosemicarbazide may be selected from the group consisting of the hydrochloride salts, sulfate salts and bifluoride salts. The $SO_2$, hydrazine or other member is added in an amount effective to reduce the oxidation potential of the resulting mixture and decompose at least a major portion of the oxidizing agent.

Aromatic fluorides prepared by the improved process of the present invention are useful as intermediates for preparing a variety of end-use products, including, for example, various pesticides, herbicides, and pharmaceuticals such as tranquilizers and the like.

DETAILED DESCRIPTION OF THE INVENTION AND OF THE MANNER AND PROCESS OF MAKING AND USING IT

In the initial step of the process of this invention, there is formed a liquid amine-HF solution comprising liquid hydrogen fluoride (HF) and, dissolved herein, the particular aromatic primary amine to be diazotized to the corresponding aromatic diazonium fluoride. In keeping with well known techniques for handling HF, the solution is preferably formed in a vessel having internal surfaces which are resistant to degradation by HF. Such surfaces may be formed, for example, of stainless steel or, preferably, teflon. The aromatic amine is added with stirring to sufficient liquid HF to prepare an amine-HF solution wherein the resulting dissolved amine remains dissolved at 0° C.

The process of the present invention may be used for all aromatic amines which are diazotizable under HF acid conditions. Such diazotizable aromatic amines include diazotizable carbocyclic aromatic primary amines (e.g. amino-benzenes) and heterocyclic aromatic primary amines (e.g. amino-pyridines), including heterocyclic aromatic primary amines containing structures wherein benzene is condensed with a heterocyclic ring. Included by such amines are carbocyclic and heterocyclic mono-amines and carbocyclic and heterocyclic polyamines (e.g. diamines). Such amines include, for example, amines derived from such carbocyclic aromatic compounds as benzene, biphenyl, diphenylmethane, diphenyl ether, condensed benzenoids such as naphthalene and anthracene, and from such heterocyclic aromatic compounds as pyridine, quinoline and isoquinoline. The aromatic ring or rings in the aromatic amines may be unsubstituted or substituted with one or more substituents selected from the group consisting of alkyl (e.g. linear or branched alkyl having 1 to 12, preferably 1 to 4, carbon atoms), alkoxy (e.g. linear or branched alkoxy having 1 to 12, preferably 1-4, carbon atoms), halo (e.g. chloro, fluoro and bromo), nitro, cyano, acyl (e.g. linear or branched acyl having 1-4 carbon atoms, such as acetyl), acylamino (e.g. acetylamino), carboxy and hydroxy.

Suitable carbocyclic aromatic primary amines include, for example, aniline; methoxyaniline (e.g., para-anisidine); chloroaniline and bromoaniline in which the chloro or bromo group is in the ortho, meta or para position relative to the amine group; toluidines such as ortho-, meta- and para-aminotoluene; and ring-halogenated (e.g., ring-chlorinated or ring-brominated) derivatives of such toluidines, e.g., 2-chloro-6-aminotoluene (also called 6-chloro-ortho-toluidine); ortho-, meta- and paraphenylene diamine; methylene dianilines such as 3,3'-, 4,4'- and 3,4'-methylene dianiline; biphenyl amines, e.g. 3,3'-diamino-biphenyl, 4,4'-diamino-biphenyl and 3,4'-diamino-biphenyl. Suitable heterocyclic aromatic primary amines include, for example, 2-, 3- and 4-aminopyridine; diaminopyridines such as 2,6-diaminopyridine; haloaminopyridines such as 2-amino-4-, 5- and 6-chloropyridine and 3-amino-5- and 6-chloropyridine; nitroaminopyridines such as 2-amino-5-nitro-pyridine; and alkylaminopyridines such as 2-amino-4-, 5- and 6-methylpyridine and 2-amino-4,6-dimethylpyridine.

In a preferred embodiment of this invention, the aromatic amine is aniline and the resulting diazotized amine is benzene diazonium fluoride, which can be decomposed to fluorobenzene (also called phenyl fluoride), which is useful as an intermediate for preparing insecticides, larvacides and tranquilizers. In another preferred embodiment, the aromatic amine is 6-chloro-ortho-toluidine and the resulting diazotized amine is 6-chloro-ortho-toluene diazonium fluoride, which can be decomposed to 2-chloro-6-fluorotoluene, which is useful as an intermediate for preparing herbicides and pharmaceuticals. In still another preferred embodiment, the aromatic amine is 4-fluoroaniline and the resulting 4-fluorobenzene diazonium fluoride can be decomposed to 1,4-difluorobenzene, which is useful as an intermediate for preparing herbicides and pharmaceuticals.

As indicated above, the amine is dissolved in a sufficient amount of HF such that the amine remains dissolved at 0° C. Such amount of HF is as follows for the indicated amines:

| Amine | Moles HF/Mole of Amine |
| --- | --- |
| Aniline | 6:1 |
| 2-chloro-o-toluidine | 6:1 |
| 4-fluoroaniline | 6:1 |
| 4,4'-Methylene dianiline | 9:1 |

The corresponding amounts for other amines can be readily determined by those skilled in the art.

A diazotization agent which contains or forms NO+ (the nitrosonium ion) is added with stirring to sufficient liquid HF to prepare a solution of nitrosyl fluoride in HF wherein the dissolved agent remains dissolved at 0° C. Suitable diazotization agents include, for example, alkali metal nitrites (e.g., sodium nitrite and potassium nitrite), nitrous halide, nitrous oxide, nitrous acid and nitrous anhydride. Sodium nitrite is preferred. An amount of HF corresponding to a ratio of at least 12 moles of HF per mole of sodium nitrite has been found sufficient. Sufficient amounts of HF for other diazotization agents can be readily determined by those skilled in the art.

The process of the present invention is based on the chemical reaction represented by the following illustrative equation:

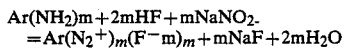
$$Ar(NH_2)_m + 2mHF + mNaNO_2$$
$$= Ar(N_2^+)_m(F^-{}_m)_m + mNaF + 2mH_2O$$

where Ar is an aromatic moiety of the aromatic mono- or polyamine $Ar(NH_2)_m$, m is an integer of 1, 2 or more and preferably is 1 or 2, and $NaNO_2$ illustrates the diazotization agent.

Hydrogen fluoride acts as both a reactant (e.g., a source of fluorine for the aromatic diazonium fluoride being prepared) and as the medium for the diazotization reaction. In order to serve as the reaction medium, there is employed an amount of HF in excess of the amount of HF required for use as such reactant. The amount of HF employed in each solution is preferably such that the total amount of HF in the amine-HF solution and nitrosyl fluoride solution introduced into the reactor results in introduction of from about (3+m) to about 30 moles and preferably from about (15+m) to 20 moles of HF per mole of introduced amine where m is the number of diazotizable - $NH_2$ groups per molecule of the amine. In general, amounts of HF less than (3+m) moles per mole of amine result in unacceptably low autothermal decomposition temperatures, thereby risking uncontrollable reaction at otherwise desirable reaction temperatures and rates and/or requiring economically unacceptable reductions in reaction temperature and rate to safeguard against such risk. Amounts of more than 30 moles of HF per mole of amine generally result in unacceptably slow preparation of aromatic diazonium fluoride and/or unacceptably high cost of HF recovery. The hydrogen fluoride may be added as aqueous hydrofluoric acid containing, for example, from about 3 to about 30 or more percent by weight of water, preferably containing at least 70 percent by weight of HF (dry basis). However, better yields and greater freedom from tar, phenols and other by-products in subsequent decomposition of the diazonium fluoride to the aromatic fluoride can be obtained by employing at least substantially anhydrous hydrogen fluoride, i.e., not containing more than about 2% by weight water, and preferably not more than 0.1% water.

The HF solution of diazotization agent is added with stirring to the HF-amine solution at a sufficiently slow rate and with sufficient cooling of the resulting reaction mixture such that the temperature of the reaction mixture is maintained from about $-10°$ C. to about $10°$ C. Alternatively, the diazotization agent may be added directly to an HF-amine solution. However, such solution should contain all the HF desired to be used. The time required for addition of the diazotization agent depends on cooling capacity and rate of diazotization. In general, such addition can be completed in from 10 minutes or less to 10 hours or more without exceeding the temperature limitation. In general, the diazotization reaction proceeds to completion within a short time (e.g. 0.5 to 2 minutes) after completion of addition of the diazotization agent. The reaction rate is temperature and concentration dependent such that a low temperature and low concentration may give a slower reaction rate and may result in incomplete diazotization.

Inasmuch as nitrosonium-ion oxidizing agent has deleterious effects on the decomposition of diazonium fluoride (as noted above), the reaction mixture should be tested for presence of oxidizing agents. If present, e.g. by virtue of excess addition of diazotization agent, contacting a sample of the reaction mixture with filter paper impregnated with a mixture of starch and potassium iodide will result in a characteristic dark blue spot on the test paper.

Where the presence of such oxidizing agent is confirmed, then in accordance with the present invention there is added to the reaction mixture a member selected from the group consisting of hydrazine, aromatic hydrazine, semicarbazide, thiosemicarbazide or an acid salt of any of the foregoing, sulfur dioxide, sodium sulfite and sodium bisulfite. The acid salt of the members hydrazine, aromatic hydrazine, semicarbazide and thiosemicarbazide preferably may be the hydrochloride salt, the sulfate salt or the bifluoride salt. The preferred aromatic hydrazine for use in the process of this invention is phenylhydrazine.

The addition of one of these agents results in a reduction of the oxidation potential of the solution by decomposing the oxidizing agent and forming gaseous by-products of nitrogen, carbon dioxide or nitric oxide. The temperature of the reaction mixture during such addition is maintained below the decomposition temperature of the diazonium fluoride and preferably below $20°$ C. Nitrogen or nitrogen and carbon dioxide or nitric oxide is rapidly formed and evolved by the resulting reaction, thereby providing a highly visible sign of the efficacy of the addition. The reaction is usually complete within seconds.

Although it is not necessary that all oxidizing agent be effectively removed by the addition of hydrazine, $SO_2$ or other selected compound, better results are obtained by complete removal of oxidizing agent. The amount of hydrazine, $SO_2$ or other compound which may be used in the process of this invention to effect complete removal of the oxidizing agent is dependent on the amount of nitrosonium-ion oxidizing agent present in the solution as determined by methods known to one skilled in the art. Since the rates and kinetics of diazotization vary depending on the amine employed, resulting in varying amounts of oxidizing agent being present, the amount of the compound required will also vary. Preferably, the hydrazine, $SO_2$ or other compound is added slowly with periodic monitoring of the reaction mixture as by the starch/potassium iodide test described above. When such test ceases to show a blue spot, removal of oxidizing agent is complete. As indicated above, it unexpectedly has been found that the presence of excess hydrazine, $SO_2$ or other selected compound in the reaction mixture does not result in a decrease of the yield of aromatic fluoride obtainable upon decomposition of the diazonium fluoride.

In the process of this invention, the discovery that these compounds are effective agents for eliminating the excess oxidizer was quite surprising. As set forth above, urea, a known reducing agent, is ineffective as an agent for eliminating the excess oxidizer in diazotization reactions. The process of the invention involves more than simply adding a reducing agent to the solution. While not wishing to be bound to a particular theory, it is believed that a reducing agent that does not bind too tightly or that is very reactive is required for the elimination of the excess oxidizer in diazotization reactions and that these additives act as scavengers which scavenge excesses of oxidizer in the diazonium hydrofluoric acid solution prior to decomposition. The compounds disclosed herein unexpectedly perform effectively in diazotization reactions, thus solving many of the known problems of these reactions.

The addition of sulfur dioxide, alkali sulfite, alkali bisulfite, or another agent which generates $SO_2$ in situ to the diazonium solution containing excess diazotizer (oxidizer) eliminates the oxidizer as evidenced by the quick evolution of nitrogen oxide and as indicated by a subsequent negative KI/starch oxidizer test. The nitrogen oxide gas evolved during the ensuing reaction is predominantly nitric oxide, but nitrous oxide and nitrogen also can be evolved.

Sulfur dioxide is one of the preferred agents in the process of this invention, although $SO_2$ would not be expected by one skilled in the art to work as a scavenging or reducing agent in this process. The use of $SO_2$ in the process of the present invention is unexpected since $SO_2$ can be used as a solvent for diazotization according to the following reaction:

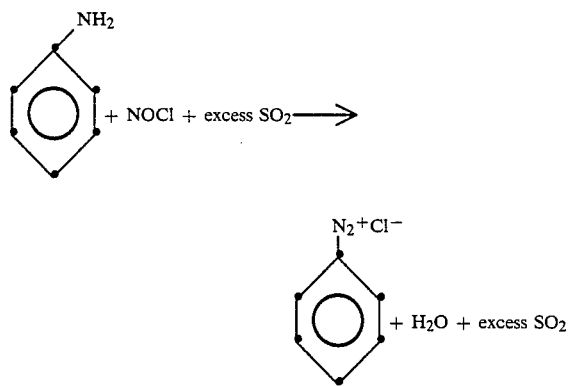

In this reaction, the acidity is low and NOCl does not react with the $SO_2$, but in the system of the present invention, $NOF(HF)=$ reacts quickly with $SO_2$.

Additionally, it is known that phenylsulfenic acid can form upon decomposition of an aromatic diazonium salt in the presence of $SO_2$. Unexpectedly, however, the yields of fluorobenzene from the process of the instant invention are unaffected by the presence of $SO_2$, which indicates that formation of phenylsulfenic acid apparently does not occur, leaving the $SO_2$ available to react with the oxidizer and remove the oxidizer from the solution.

When $SO_2$ is used, it may be added as a gas, liquid, or solution in $H_2O$, HF and/or $H_2SO_4$. As it is preferred to minimize the amount of $H_2O$ in the solution, the preferred method for adding $SO_2$ to the diazonium solution is as a gas by a continuous regulated system after diazotization of the aromatic amine. The $SO_2$ gas may be added from a regulated gas cylinder of $SO_2$ gas into an inline mixer where liquid diazonium contacts the $SO_2$ gas. When $SO_2$ is used in the process of this invention, it is believed that the $NOF.(HF)_x$ (nitrosyl fluoride in HF) formed by adding sodium nitrite to hydrogen fluoride (liquid) reacts with $SO_2$ to result in the following reaction equation:

$$2NOF.(HF)_x + SO_2 + 2H_2O \rightarrow 2NO(g) + H_2SO_4 + 2(x+1)HF$$

The use of $SO_2$ in this process does not result in any unwanted by-products.

An agent which generates $SO_2$ in situ also may be used and will effectively eliminate excess oxidizer. Agents which generate $SO_2$ in situ include alkali sulfite and alkali bisulfite, preferably sodium sulfite or sodium bisulfite. In aqueous solution, the addition of sodium sulfite or sodium bisulfite to a diazonium salt would generally result in its reduction to the phenylhydrazine, as in the following reaction:

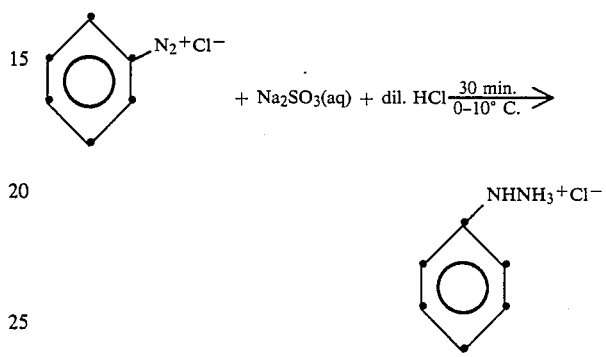

However, phenylhydrazine cannot be detected in the solution resulting from the addition of sodium sulfite or sodium bisulfite in the process of the present invention. This is true even when $SO_2$ is used as a co-solvent with HF. These compounds generate $SO_2$ in situ when dissolved in a strong acid, such as HF. These agents may be added to the solution in solid form.

Another of the preferred additives is hydrazine, which may be used in hydrated form such as the commercially available form containing approximately 85 percent by weight water. While hydrazine is only sparingly soluble in HF, it has unexpectedly been found to be highly reactive in the HF solutions of the present invention. Hydrazine has a considerable heat of solvation in HF. Accordingly, hydrazine is preferably used in hydrated form and initially mixed with water (e.g. in about 1:1 weight ratio) prior to addition to the reaction mixture. More preferably, the aqueous mixture is diluted by separately mixing HF (e.g. 4 parts HF per one part of aqueous mixture) and, after cooling, the resulting mixture is added to the reaction mixture containing the oxidizing agent to be treated.

After treatment with the agent for eliminating the oxidizer in the diazonium solution, the reaction mixture is warmed by application of external heat to a sufficient temperature to form the aromatic fluoride with evolution of gaseous nitrogen. The rate of warming or heating is preferably moderated to avoid violent evolution of nitrogen, i.e., avoiding such rapid nitrogen evolution that liquid reaction mixture would be entrained in the nitrogen gas exiting the reaction vessel. For the same purpose and to increase the yield of the aromatic fluoride being formed, the temperature of the reaction mixture during conversion of the diazonium fluoride to the aromatic fluoride is preferably not permitted to exceed that temperature at which violent evolution of nitrogen would occur. If the aromatic amine is aniline, for example, such temperature is about 45° C. The corresponding temperature for other aromatic amines can be readily determined by routine observation. Decomposition time may vary from 0.5 seconds or less to 25 hours or more. The various reactions are preferably conducted at atmospheric pressure in a type 304 stainless steel reactor.

The resulting aromatic fluoride product may conveniently be recovered from the reaction mixture by decanting the organic phase directly either with or without a co-solvent and distilling or steam distilling the aromatic fluoride after neutralization.

Practice of the present invention is further illustrated by the following non-limiting examples. All parts and percentages given throughout this disclosure, including the examples and appended claims, are by weight unless otherwise indicated.

EXAMPLE 1

To a 4-oz. polyethylene bottle (4 fluid ounces) cooled to $-15°$ C. was charged liquid anhydrous HF, 4.88 moles, 97.6 grams (g), followed by slow addition of aniline (0.7655 mole, 71.29 g) with stirring and cooling, thereby preparing a solution of aniline in HF (the "aniline-HF solution"). To another 4-oz. polyethylene bottle cooled to $-15°$ C. was charged liquid anhydrous HF (9.28 moles, 185.6 g), followed by incremental addition of granular sodium nitrite (0.8030 mole, 55.41 g) with stirring and cooling. The resulting solution of nitrosyl fluoride in HF (containing approximately 0.8030 mole of nitrosonium-ion diazotization agent) was slowly added with stirring to the aniline-HF solution (0.7655 mole of aniline) while maintaining the temperature of the resulting diazotizatin-reaction mixture slightly below 10° C.

The resulting reaction mixture contained benzene diazonium fluoride as a solute in hydrofluoric acid. Testing with KI-starch solution showed that the mixture contained at least one oxidizing agent and was strongly oxidizing, i.e. characterized with appreciable oxidation potential. The theoretical (stoichiometric) amount of benzene diazonium fluoride was 0.7655 mole (i.e., equal to the molar amount of the 0.7655 mole aniline, the limiting reactant due to the addition of excess sodium nitrite), which corresponds to 395.9 g of the diazonium fluoride. Two samples of the mixture were taken, hereinafter referred to as Mixture A and Mixture B, in amounts corresponding to, respectively, 273.8 g (0.5294 mole) and 11.41 g (0.2231 mole) of the theoretical amount of benzene diazonium fluoride. The two mixtures were treated as follows.

Mixture A

Mixture A was heated to 40° C. in a 2-liter Parr reactor for 2½ hours to decompose the diazonium fluoride. After standing overnight, the reactor was cooled to 0° C. and slowly vented. The resulting black mixture was transferred to a teflon separatory funnel. The resulting dark purple organic phase separated very slowly from the black HF phase. The organic phase was observed to be essentially filled with a purple tar-like material. There were recovered from the separatory funnel 71.55 g (63.5 ml) of organic phase and 169.66 g (130 ml) of HF phase.

The liquid in the organic phase was decanted, thereby yielding a tar-like emulsion (48.2 g, 40.5 ml) and decanted organic liquid (23.35 g, 23 ml). The weight "loss" (17.8 g) was attributed to tar hold-up on the reactor wall. Based on analysis of the organic liquid phase by HPLC (i.e., high performance liquid chromatography), fluorobenzene was obtained in an amount of about 22.8 g (0.237 mole), a 44.8% yield based on aniline.

Mixture B

To Mixture B in a poly-bottle was added with stirring hydrazine sulfate (2.0 g, 0.015 mole) at a mixture temperature of about 5°-10° C. There was an immediate evolution of nitrogen, which was essentially complete at the end of a 2-minute period. Excess hydrazine sulfate formed a layer on the bottom of the poly-bottle. Testing with KI-starch solution indicated absence of oxidizing agents. The resulting mixture was poured into a 450-ml Parr reactor and thereafter heated at 45° C. until evolution of nitrogen ceased, thereby decomposing the diazonium fluoride. The reactor was thereafter cooled and slowly vented. The resulting mixture was poured into a teflon separatory funnel. Upon standing for a brief period, the mixture separated into an organic phase and an HF phase. The organic phase was light brown and clearly delineated from the dark brown HF phase.

There were recovered from the separatory funnel 19.75 g (20 ml) of organic liquid phase and 87.76 g (67.5 ml) of HF phase. Based on analysis of both phases by H.P.L.C., fluorobenzene was obtained in a total amount of about 19.65 g (0.2044 mole), a 91.6% yield based on aniline.

EXAMPLE 2

Benzene diazonium fluoride (98.62 g, 0.1877 mole) was prepared in HF substantially in accordance with the procedure of Example 1 using a 5% overcharge of sodium nitrite (0.648 g, 0.00939 mole). Urea (2.21 g, 0.0368 mole) was added, to the resulting diazotized product mixture with stirring at 5° C. for 15 minutes. Thereafter, testing with KI-starch solution showed that the mixture continued to contain at least one oxidizing agent and continued to be strongly oxidizing, i.e. characterized with appreciable oxidation potential. The urea-treated mixture was poured into a 450-ml Parr reactor and thereafter heated to 46° C. until evolution of nitrogen ceased, thereby decomposing the diazonium fluoride. The reactor was thereafter cooled and slowly vented. The resulting mixture was poured into a teflon separatory funnel. Upon standing for a brief period, the mixture was observed to be similar to the mixture resulting from the decomposition step for Mixture A in Example 1, including presence of a black tarlike emulsion of the resulting HF phase in the resulting organic phase.

EXAMPLE 3

Benzene diazonium fluoride (130.04 g, 0.2475 mole) was prepared in HF substantially in accordance with the procedure of Example 1 using 5% excess sodium nitrite. Hydrazine hydrate (85%) (1.00 g, 0.0266 mole) was diluted 1:1 with 1.00 g of deionized water, and the resulting mixture was added to anhydrous HF (9.51 g, 0.476 mole) while cooling in a dry ice methanol bath. The hydrazine-HF solution (11.45 g) was added all at once to the benzene diazonium fluoride solution. Nitrogen evolution took place over a period of less than a minute. Thereafter, testing with KI-starch solution showed absence of oxidizing agent in the mixture. Next, decomposition of the diazonium fluoride was effected substantially in accordance with the procedure of Example 2. The resulting mixture was poured into a teflon separating funnel. Upon standing for a brief period, the mixture separated into two clear brown phases (an organic phase and an HF phase).

There were recovered from the separatory funnel 20.89 g (21 ml) of organic phase and 110.86 g (86 ml) of HF phase. Based on analysis of both phases by HPLC, fluorobenzene was obtained in a total amount of about 22.20 g, (0.2309 mole), a 93.3% yield based on aniline.

EXAMPLE 4

Benzene diazonium fluoride was prepared in HF substantially in accordance with the procedure of Example 1. HPLC analysis of the resulting mixture by beta-naphthol coupling indicated a concentration of 0.001984 mole of the diazonium fluoride per gram of mixture. Testing with KI-starch solution showed that the mixture contained at least one oxidizing agent and was strongly oxidizing, i.e. characterized with appreciable oxidation potential.

A 65.48 g, 0.130 mole sample of the mixture was treated with thiosemicarbazide hydrochloride (0.05 g, 0.00039 mole). Thereafter, testing with KI-starch solution showed absence of oxidizing agent in the mixture. Next, decomposition of the diazonium fluoride was effected substantially in accordance with the procedure of Example 2. The resulting mixture was poured into a teflon separating funnel. Upon standing for a brief period, the mixture separated into two brown phases (an organic phase and an HF phase).

There were recovered from the separatory funnel 10.24 g (10 ml) of organic phase and 49.91 g (39 ml) of HF phase. Based on analysis of both phases by HPLC, fluorobenzene was obtained in a total amount of about 10.20 g (0.1061 mole), an 81.6% yield based on aniline.

EXAMPLE 5

Aniline (75.37 g, 0.8093 mole) in liquid hydrogen fluoride (101.6 g, 5.08 mole) was diazotized by the dropwise addition of a solution of sodium nitrite (56.47 g, 0.8184 mole) in liquid hydrogen fluoride (216.4 g, 10.82 moles). The temperature of diazotization was maintained below 15° C. with an ice bath. Twenty minutes after the addition of all the nitrite solution, a KI/starch solution test on the resultant solution indicated the presence of unreacted nitrite. The diazonium solution (421.40 g) was poured into a 2 Liter Parr reactor. The reactor was sealed and placed in a 40° C. water bath. The stirring rate was 300–400 rpm which was maintained for two hours. The reactor was left standing to cool. Nitrogen was slowly vented so as to minimize the HF loss. The reactor was opened and the contents were poured into a 1 liter P.F.A. separatory funnel. The two phases were separated. The light green HF phase (313.33 g, 245 ml) was drained into a tared plastic 500 ml graduated cylinder. The brown organic phase contained some dark brown polymeric material ("diazo tars"). The whole organic phase containing the polymeric material weighed 76.80 g (75.5 ml). The crude fluorobenzene was decanted free of the liquid polymer. The organic liquid decanted weighed 63.71 g (63.5 ml), and by difference the wetted polymer weighed 13.09 g, occupying a volume of 12.0 ml. The liquid was drawn from the wetted polymer by vacuum filtration through a 5 micron T.F.E. filter. A brown solid 10.49 g remained which smelled of the fluorobiphenyl by-products. Both organic and HF phases made-up the filtrate. The filtrate (6.85 g) was placed into a P.F.A. separatory funnel. The layers were separated into tared polybottles. The weight of the organic and HF phases were 2.48 g and 4.35 g, respectively, with evaporative losses accounting for 5.77 g. A small sample of the brown polymeric solid was taken for HPLC. The remainder was sequentially washed with dichloromethane, methanol, and water which afforded 0.14 g of tan amorphous solid after drying.

Each phase from the filtrate was combined with its respective reaction layer. Samples of the combined crude HF and organic phases were diluted in methanol HPLC analysis. Fluorobenzene content was as follows: HF phase contained 0.13 g, 0.0013 mole; organic phase contained 61.66 g., 0.642 mole; and the polymer sample contained 0.036 g, 0.00037 mole. The total fluorobenzene accounted for was 61.83 g, 0.643 mole for a 79.5% yield from aniline. The total mass accountability from the diazonium solution added to the reactor was 96.7%.

EXAMPLE 6

To an aniline (21.26 g, 0.2283 mole) solution with liquid hydrogen fluoride (27.5 g, 1.38 mole) as solvent was added dropwise a solution of sodium nitrite (16.90 g, 0.245 mole) in liquid hydrogen fluoride (50–0 g, 2.50 moles). The temperature of the resulting diazotization was maintained below 15° C. by cooling the polyethylene container in an ice bath with stirring. Fifteen minutes after the addition of all the nitrite solution, a small aliquot of the diazonium solution was added to an aqueous solution of potassium iodide and starch. The KI/starch solution turned black indicating excess nitrite. To the diazonium solution was transferred sulfur dioxide ($SO_2$) (1.4 g, 0.022 mole) from a lecture bottle. Outgassing was noted to occur from the solution. The KI/starch test was now negative. The diazonium solution (117.5 g) was poured into a 450 ml Parr reactor. The reactor was sealed and heated until the dediazotization became autogeneous as indicated by the temperature and pressure rise. The reactor was cooled to below room temperature in an ice bath. The nitrogen was slowly vented to minimize the hydrogen fluoride loss. The contents of the reactor were poured into a P.F.A. separatory funnel. The light green HF phase (86.26 g) and light brown crude fluorobenzene phase (20.04 g) were separated into tared polyethylene bottles. Samples of each phase were neutralized in 100 ml volumetric flasks containing methanol for analysis by high pressure liquid chromatography equipped with a UV detector at 254 nanometers. The concentration of the product fluorobenzene was measured relative to an external standard using a digital integrator to compare area count. The yield of fluorobenzene from aniline was 85.0% with 4.1% of the total mass lost in transfers.

BEST MODE CONTEMPLATED

The best mode contemplated for carrying out this invention has been set forth in the above description, for example, by way of setting forth preferred materials and operating conditions, including but not limited to preferred ranges and values of amounts and other nonobvious variables material to successfully practicing the invention in the best way contemplated at the time of executing this patent application.

It is understood that the foregoing detailed description is given merely by way of illustration and that many modifications may be made therein without departing from the spirit or scope of the present invention.

What is claimed:

1. In a diazotization-fluorination process for preparing an aromatic fluoride from a corresponding diazotizable aromatic primary amine wherein (A) the amine is diazotized in a reaction mixture comprising (i) a reaction medium consisting essentially of hydrogen fluoride, (ii) said amine and (iii) a nitrosonium ion-containing or -generating diazotizing agent under reaction conditions such that the resulting reaction mixture comprising the resulting aromatic diazonium fluoride further comprises one or more oxidizing agents, whereby said resulting reaction mixture produces oxidant-indicating blue color on test paper impregnated with starch and potassium iodide, and (B) the aromatic diazonium fluoride is decomposed at elevated temperature in said resulting reaction mixture to nitrogen and the aromatic fluoride, the improvement which comprises, prior to decomposing said diazonium fluoride, adding to said resulting mixture a member selected from the group consisting of hydrazine, aromatic hydrazine, semicarbazide, thiosemicarbazide, acid salts thereof, sulfur dioxide, sodium sulfite, and sodium bisulfite, said member being added in an amount effective to reduce the oxidation potential of said resulting mixture and substantially decompose said agent.

2. The process of claim 1 wherein the acid salts of hydrazine, semicarbazide, and thiosemicarbazide are selected from the group consisting of their hydrochloride salts, sulfate salts and bifluoride salts.

3. The process of claim 1 or 2 wherein said member is added in an amount sufficient to reduce said oxidation potential to zero.

4. The process of claim 3 wherein the added amount of said member exceeds the amount required to reduce said oxidation potential to zero.

5. The process of claim 1 wherein said member is hydrazine.

6. The process of claim 5 wherein the hydrazine is hydrated.

7. The process of claim 6 wherein the hydrazine is added as an aqueous solution thereof.

8. The process of claim 7 wherein said solution further comprises HF.

9. The process of claim 1 wherein said member is hydrazine sulfate.

10. The process of claim 1 wherein said member is thiosemicarbazide or an acid salt thereof.

11. The process of claim 10 wherein said member is thiosemicarbazide hydrochloride.

12. The process of claim 1 wherein said member is sulfur dioxide.

13. The process of claim 12 wherein said sulfur dioxide is added as a gas.

14. The process of claim 1 wherein said member is sulfur dioxide formed in situ by the addition of sodium sulfite or sodium bisulfite.

15. The process of claim 1 wherein said member is phenylhydrazine.

* * * * *

UNITED STATES PATENT AND TRADEMARK OFFICE
CERTIFICATE OF CORRECTION

PATENT NO. : 4,886,920

DATED : December 12, 1989

INVENTOR(S) : Gary L. Cantrell

It is certified that error appears in the above-identified patent and that said Letters Patent is hereby corrected as shown below:

On the title page, item [57]:
In the Abstract, line 10, "sulfate" should be --sulfite--.

Col. 7, line 43, "NOF(HF)=" should be --$NOF(HF)_x$--.

Col. 9, line 31, "diazotizatin-reaction" should be --diazotization-reaction----diazotization-reaction--.

Col. 9, line 46, "11.41 g" should be --115.41 g--.

Signed and Sealed this

Twenty-third Day of July, 1991

Attest:

HARRY F. MANBECK, JR.

*Attesting Officer*  *Commissioner of Patents and Trademarks*